(12) United States Patent
Thran

(10) Patent No.: US 11,324,473 B2
(45) Date of Patent: May 10, 2022

(54) CARDIAC COMPUTED TOMOGRAPHY

(71) Applicant: KONINKLIJKE PHILIPS N.V., Eindhoven (NL)

(72) Inventor: Axel Thran, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 565 days.

(21) Appl. No.: 16/329,797

(22) PCT Filed: Sep. 4, 2017

(86) PCT No.: PCT/EP2017/072038
§ 371 (c)(1),
(2) Date: Mar. 1, 2019

(87) PCT Pub. No.: WO2018/046413
PCT Pub. Date: Mar. 15, 2018

(65) Prior Publication Data
US 2019/0192104 A1 Jun. 27, 2019

(30) Foreign Application Priority Data
Sep. 8, 2016 (EP) .................................... 16187741

(51) Int. Cl.
| | | |
|---|---|---|
| *A61B 6/00* | (2006.01) | |
| *A61B 6/03* | (2006.01) | |
| *A61B 5/352* | (2021.01) | |
| *A61B 5/024* | (2006.01) | |
| *G06F 17/18* | (2006.01) | |

(52) U.S. Cl.
CPC .......... *A61B 6/541* (2013.01); *A61B 5/02405* (2013.01); *A61B 5/352* (2021.01); *A61B 6/032* (2013.01); *A61B 6/503* (2013.01); *G06F 17/18* (2013.01); *A61B 6/5205* (2013.01)

(58) Field of Classification Search
CPC ..... A61B 5/02405; A61B 5/352; A61B 6/032; A61B 6/503; A61B 6/5205; A61B 6/541; G06F 17/18
See application file for complete search history.

(56) References Cited

U.S. PATENT DOCUMENTS

| | | |
|---|---|---|
| 7,313,213 B1 | 12/2007 | Hsieh |
| 2003/0092983 A1 | 5/2003 | Baker |
| 2005/0187587 A1 | 8/2005 | Burrell |

(Continued)

OTHER PUBLICATIONS

Desjardins, et al.: "ECG-Gated Cardiac CT", American Journal of Roentgenology, Jan. 1, 2004.

(Continued)

*Primary Examiner* — Mark D Remaly
(74) *Attorney, Agent, or Firm* — Larry Liberchuk

(57) ABSTRACT

A method for operating a cardiac CT imaging system (200) in coronary CT with prospective electrocardiography-triggering of the imaging system (200) is proposed. The method comprises the steps of determining a plurality of R-peak times (ti) from a dataset of electrocardiography data, determining a variability of a heart rate by statistically analyzing the determined R-peak times (ti), and automatically adjusting an acquisition time period ($\Delta T_{ac}$) of the CT imaging system (200) for acquiring projection data based on the determined variability of the heart rate.

20 Claims, 2 Drawing Sheets

(56) References Cited

U.S. PATENT DOCUMENTS

2006/0287594 A1  12/2006  Boese

OTHER PUBLICATIONS

Labounty, et al.: "Effect of Padding Duration on Radiation Dose and Image Interpretation in Prospectively ECG-Triggered Coronary CT Angiography", AJR:194, Apr. 2010.
Matthew J. Budoff: "Maximizing dose reductions with cardiac CT", Int J Cardiovasc Imaging (2009) 25:279-287.

CARDIAC COMPUTED TOMOGRAPHY

CROSS REFERENCE TO RELATED APPLICATIONS

This application is the U.S. National Phase application under 35 U.S.C. § 371 of International Application No. PCT/EP2017/072038 filed Sep. 4, 2017, published as WO 2018/046413 on Mar. 15, 2018, which claims the benefit of European Patent Application Number 16187741.0 filed Sep. 8, 2016. These applications are hereby incorporated by reference herein.

FIELD OF THE INVENTION

The invention generally relates to cardiac computed tomography (CT). More specifically, the invention relates to a method for operating a cardiac CT imaging system, to a cardiac CT imaging system, to a computer program element and to a computer-readable medium.

BACKGROUND OF THE INVENTION

Modern computed tomography imaging systems utilized for imaging a heart, e.g. for coronary CT and/or for coronary CT angiography, are usually based on electrocardiography (ECG) data for determining an acquisition time and/or an acquisition time period, in which projection data and/or scan data are acquired by means of the CT imaging system. During these so-called ECG-triggered cardiac CT scans, such as e.g. step and shoot scans and/or helical scans, projection data of the heart are optimally acquired at certain heart phases, in which a motion of the heart is minimal. Therein, ECG triggering may mean, that the data acquisition is started at a certain time after the last detected R-peak of a heart cycle or cardiac cycle, respectively. For instance, for a late diastole acquisition, the projection data may be acquired at an aimed heart phase near 75% of the heart cycle, i.e. around 75% between two consecutive R-peaks.

However, when the time point of the next R-peak deviates from the expected time point calculated e.g. from a mean heart rate, the scan data may be acquired over a different heart phase. Accordingly, a trade-off has to be found between minimizing a radiation dose delivered to a patient and ensuring that the data are acquired over a sufficiently long acquisition time period centered around an aimed heart phase.

An optimal range of projection angles, in which projection data are acquired, may depend on a stability of the heart rate. For a rather stable heart rate the projection data acquired for each shoot may encompass an angle range only slightly larger than a range sufficient for an image reconstruction. In contrast, for an instable heart rate projection data may have to be acquired over a larger angle range and thus over a longer acquisition time period. This may mean that the acquisition time period, may have to be increased by a safety margin, the so-called padding, padding time and/or padding time period. This may allow an adjustment of the projection angle ranges used for image reconstruction, but also results also results in increase of dose.

SUMMARY OF THE INVENTION

There may therefore be a need for reducing and/or minimizing a dose while improving an image quality in cardiac computed tomography (CT), such as coronary CT and/or coronary CT angiography.

The object of the present invention is solved by the subject matter of the independent claims, wherein further embodiments are incorporated in the dependent claims and the following description.

According to a first aspect of the invention, a method for operating a cardiac CT imaging system is provided. The method for operating the cardiac CT imaging system particularly relates to coronary CT with prospective electrocardiography-triggering (ECG-triggering) of the imaging system. This may mean, that a data acquisition by means of the imaging system may be started at a certain time after an R-peak of a heart cycle, which is determined based on ECG data and/or based on a dataset comprising ECG data.

The method for operating the cardiac CT imaging system comprises the steps of:

determining a plurality of R-peak times $t_i$ from a dataset of electrocardiography data;
  determining a variability of a heart rate by statistically analyzing the determined R-peak times $t_i$; and
  automatically adjusting an acquisition time period $\Delta T_{ac}$ of the CT imaging system for acquiring projection data based on the determined variability of the heart rate.

Rephrasing the first aspect, a dataset comprising ECG data, such as e.g. an electrocardiogram, may be acquired. This may be accomplished for instance by measuring the electrical potential of the heart with electrodes as a function of time by means of an electrocardiograph and/or an ECG device. The dataset may comprise at least three R-peaks (or signals/data relating to R-peaks), for example at least five, and particularly at least ten R-peaks. Based on this dataset and/or based on these data the R-peaks may be determined, wherein R-peaks generally refer to dominant deflections in the ECG data which are usually recognizable as heart beat. Further, the time instants of these R-peaks, i.e. the R-peak times may then be determined and e.g. stored on a data storage of the CT imaging system. Usually, a heart cycle time and/or a cardiac cycle time, which may denote a time period between two consecutive R-peaks, varies somewhat from heart cycle to heart cycle due to the fact that the heart rate is not perfectly constant. Accordingly, the variability of the heart rate may refer to an inhomogenity in the time intervals between R-R peaks and/or it may refer to deviations from a mean heart rate.

During a cardiac CT scan this variability of the heart should be compensated and/or taken into account in order to acquire sufficient projection data of the heart at a certain heart phase, which allows comprehensive reconstruction of the heart from the acquired projection data.

The state-of-art approach to compensate the heart rate variability is to extend an acquisition time period by the so-called padding and/or padding time. This padding time relates to a safety margin to ensure that projection data may be acquired at the certain heart phase. The padding time is usually specified and manually set by a user (e.g. a physician) of the CT imaging system before the actual cardiac CT scan is started. Accordingly, in some cases the padding time may be too long and inappropriate, because e.g. an actual variability of the heart rate may be less than assumed by the user. This may result in an unnecessarily high radiation dose.

In contrast to this approach, according to the invention the variability of the heart rate may be determined by statistically analyzing the determined R-peak times. This may mean that statistics are applied to a distribution of the determined R-peak times, which may allow to precisely estimate and/or determine the variability of the heart rate. Further, as the R-peak times may be statistically analyzed e.g. by means of a controller of the CT imaging system, this statistical analysis may be performed using ECG data acquired directly and/or immediately before acquiring projection data by means of the CT imaging system. Also, the statistical analysis may be performed real-time during the actual CT scan, i.e. while acquiring projection data. This may allow to account for short-term changes in the variability of the heart rate.

Further, according to the invention the acquisition time period may automatically be adjusted and/or set by the CT imaging system and/or a controller thereof. Therein, the term "automatically adjusting" may comprise an automated adjustment by means of a controller, e.g. based on a feedback control for determining the variability of the heart and setting the acquisition time period accordingly.

This advantageously allows to minimize the acquisition time period according to a current variability of the heart rate. Thus, advantageously the dose may be reduced by taking a current heart rate variability of a patient into account.

According to an example, automatically adjusting the acquisition time period based on the determined variability of the heart rate comprises automatically adjusting a length of the acquisition time period based on the determined variability of the heart rate. In other words, automatically adjusting the acquisition time period may comprise increasing and/or decreasing a length of the acquisition time period based on the determined variability of the heart rate. According to a further example, automatically adjusting the acquisition time period may also comprise determining a trigger time point, at which an acquisition of projection data by means of the CT imaging system may be started.

According to an embodiment, the step of statistically analyzing the R-peak times $t_i$ comprises determining a plurality of heart cycle times based on the determined R-peak times $t_i$. Therein, the heart cycle times may relate to R-R interval times, i.e. to a time between two consecutive R-peaks and may be expressed as $\Delta T = t_i = t_i - t_{i-1}$, with i=1 ... N denoting a number of R-peaks. In other words, the variability of the heart rate may be determined based on determining a plurality of heart cycle times.

Alternatively or additionally, the step of statistically analyzing the R-peak times $t_i$ comprises determining a plurality of differences of consecutive heart cycle times based on the determined R-peak times $t_i$. The differences of consecutive heart cycle times may be expressed as $\Delta T_{i+1} - \Delta T_i$, with i=1 ... N denoting a number of R-peaks. In other words, the variability of the heart rate may be determined based on determining a plurality of differences of consecutive heart cycle times.

This way, the variability of the heart rate may be determined and/or analyzed, and the acquisition times as well as the dose may advantageously be reduced, particularly for stable heart rates. Further, the heart rate may increase e.g. when an injection of contrast agent is performed and/or started. This effect may advantageously be taken into account by analyzing the differences of heart cycle times of consecutive heart beats, i.e. R-peaks.

According to an embodiment, the step of statistically analyzing the R-peak times $t_i$ further comprises determining a standard deviation of the determined plurality of heart cycle times. In other words, the variability of the heart rate may be determined based on the standard deviation of the determined plurality of heart cycle times. The standard deviation may be expressed as $\sigma = \mathrm{std}(\{t_i - t_{i-1} | i=1 \ldots N-1\}) = \sqrt{\mathrm{var}(t_i - t_{i-1})}$, with $\mathrm{var}(t_i - t_{i-1})$ being the variance. The standard deviation of the determined plurality of heart cycle times may provide a comprehensive and accurately determinable measure for the variability of the heart.

Alternatively or additionally, the step of statistically analyzing the R-peak times $t_i$ further comprises determining a standard deviation of the determined plurality of differences of consecutive heart cycle times. In other words, the variability of the heart rate may be determined based on the standard deviation of the determined plurality of differences of consecutive heart cycle times. This standard deviation may be expressed as $\sigma = \mathrm{std}(\{\Delta T_{i+1} - \Delta T_i | i=2 \ldots N-1\}) = \sqrt{\mathrm{var}(\Delta T_{i+1} - \Delta T_i)}$, with $\mathrm{var}(\Delta T_{i+1} - \Delta T_i)$ being the variance. Also the standard deviation of the determined plurality of differences of consecutive heart cycle times may provide a comprehensive and accurately determinable measure for the variability of the heart.

According to an embodiment, the method further comprises the step of determining a padding time $\Delta T_{pad}$ by multiplying the standard deviation of the plurality of heart cycle times and/or the standard deviation of the plurality of differences of consecutive heart cycle times by a phase factor $\gamma$ relating to and/or proportional to a heart phase $\varphi$ of the heart cycle. In other words, the padding time $\Delta T_{pad}$ may be determined based on a multiplication of the standard deviation of the plurality of heart cycle times and/or the standard deviation of the plurality of differences of consecutive heart cycle times with the phase factor. The padding time may denote a time and/or a time period by which the acquisition time period $\Delta Tac$ may be increased, wherein the padding time may be added to the beginning and/or the end of acquisition time period. Accordingly, the method may further comprise the step of increasing the acquisition time period by the padding time. The heart phase may denote any phase of the heart cycle, i.e. between two consecutive R-R peaks. Generally, the heart phase may denote a phase of the heart cycle around which and/or centered around which projection data are to be acquired. Usually, the heart phase is expressed in percent of a complete heart cycle, such as e.g. 75%. The heart phase may be predefined and/or definable. The heart phase may also be programmable and/or settable, e.g. by a user and/or automatically by a controller of the CT imaging system. This may allow to adjust settings of the CT imaging systems according to specific needs.

According to an embodiment, the phase factor $\gamma$ is between 0.65 and 0.85 relating to a heart phase $\varphi$ of 65% to 85% of the heart cycle. Preferably, the phase factor may be between 0.7 and 0.8, for instance 0.75. Correspondingly, the heart phase may be between 70% and 80%, e.g. 75%. At this so-called aimed heart phase, around which acquisition data and/or acquired projection data should be centered, a motion of the heart may be minimal, which may allow to acquire reliable projection data and/or which may allow to avoid artifacts in the imaging data potentially induced by movement of the heart during the acquisition time period. Accordingly, acquiring projection data near the above-mentioned heart phase may improve reconstruction of a heart image based on acquired projection data.

According to an embodiment, the phase factor $\gamma$ is between 0.3 and 0.5 relating to a heart phase $\varphi$ of 30% to 50% of the heart cycle. Preferably, the phase factor may be between 0.35 and 0.45, for instance 0.4. Correspondingly, the heart phase may be between 35% and 45%, e.g. 40%. Also at this heart phase a motion of the heart may be minimal, which may allow to acquire reliable projection data and/or which may allow to avoid artifacts in the imaging data potentially induced by movement of the heart during the acquisition time period, and accordingly acquiring projection data near the above-mentioned heart phase may improve reconstruction of a heart image based on acquired projection data.

According to an embodiment, the method further comprises determining the padding time $\Delta T_{pad}$ by multiplying the standard deviation of the plurality of heart cycle times and/or the standard deviation of the plurality of differences of consecutive heart cycle times by the phase factor $\gamma$ and a confidence factor $\mu$ indicative of and/or relating to a probability of acquiring projection data sufficient and/or required for a reconstruction of the heart at the heart phase $\varphi$, e.g. precisely at the predefined heart phase. In other words, the padding time $\Delta T_{pad}$ may be determined based on a multiplication of the standard deviation of the plurality of heart cycle times and/or the standard deviation of the plurality of differences of consecutive heart cycle times with the phase factor $\gamma$ and the confidence factor $\mu$. This way it may be ensured that in a certain percentage of cases, which may be indicated by the confidence factor, sufficient projection data are acquired centered around the aimed heart phase, i.e. before and after the aimed heart phase, allowing comprehensive reconstruction of the heart.

According to an embodiment, the method further comprises comparing the standard deviation of the plurality of heart cycle times and/or the standard deviation of the plurality of differences of consecutive heart cycle times with a threshold value of the respective standard deviation. Therein, the acquisition time period $\Delta T_{ac}$ is only increased by the padding time $\Delta T_{pad}$ if the standard deviation of the plurality of heart cycle times and/or the standard deviation of the plurality of differences of consecutive heart cycle times exceeds the threshold value. Slight deviations of the acquisition time period from the predefined heart phase, e.g. 75%, during a CT scan may have no considerable impact on the image quality. Accordingly, in these cases the acquisition time period may not be increased and the dose may be further reduced. This may be taken into account by comparing the standard deviation to the threshold and only increasing the acquisition time period by the padding time if the threshold is exceeded.

According to an embodiment, the confidence factor $\mu$ is determined under the assumption that a random variable X describes a variation of the heart cycle times and/or describes a variation of the plurality of differences of consecutive heart cycle times. Alternatively or additionally the confidence factor $\mu$ is determined based on a confidence level of a probability distribution assumed for a random variable X describing a variation of the heart cycle times and/or a variation of the plurality of differences of consecutive heart cycle times. The random variable may have any kind of probability distribution, such as e.g. a Gaussian distribution, a Bernoulli distribution, a Lagrange distribution, a Poisson distribution or the like. Accordingly, the variable X may be e.g. a Gaussian distributed, a Bernoulli distributed, a Lagrange distributed, a Poisson distributed variable. By assuming a certain probability distribution for a random variable, an appropriate confidence factor may be determined, which may in turn ensure that in most cases an appropriate acquisition time period is chosen.

According to an embodiment, the random variable X is a Gaussian distributed random variable.

According to an embodiment, the confidence factor $\mu$ is determined based on percentiles of a Gaussian function p(t) describing a probability distribution of a heart phase $\varphi$ within the heart cycle, wherein the Gaussian function p(t) has a standard deviation of $\gamma \cdot \sigma$. By way of example, assuming that the Gaussian distributed random variable X describes the variation of the differences of consecutive heart cycle times, a probability distribution of a next R-peak time $t_{i+1}$ may be estimated by $t_{i+1}=t_i+(t_i-t_{i-1})+X$. The probability distribution for time $t_i^\varphi$, which may denote a phase point and/or a phase time point, at a certain heart phase $\varphi$ within the heart cycle is correspondingly a Gaussian function with a standard deviation of $\gamma \cdot \sigma$, centered around $t=t_i^\varphi$ and may be expressed as $$p(t = t_i^\varphi) = C \cdot \exp\left(\frac{-(t - (t_i + \gamma \cdot (t_i - t_{i-1})))^2}{2(\gamma \cdot \sigma)^2}\right).$$

Therein, C is a normalization factor. Accordingly, the padding time, i.e. the additional acquisition time needed to achieve sufficient data centered around the heart phase $\varphi$, can be calculated from the quantiles of this distribution. This allows to statistically determine, adjust and/or set an appropriate acquisition time period and/or padding time, thereby ensuring that in a reasonable number of CT scans sufficient projection data may be acquired.

According to an embodiment, the percentiles of the Gaussian function p(t) are 2.5% and 97.5%, which relates to a confidence level of 95%. This may ensure that in a reasonable number of CT scans sufficient projection data may be acquired.

According to an embodiment the method further comprises acquiring a dataset comprising electrocardiography data. These data may be acquired e.g. by means of an electrocardiograph and/or a ECG device.

A second aspect of the invention relates to a cardiac CT imaging system, comprising an X-ray radiation source, an X-ray detector and a controller, wherein the controller is configured to perform any of the steps of the method as described above and in the following.

It has to be understood that features of the method as described above and in the following may be features of the CT imaging system as described above and in the following. Vice versa, features of the CT imaging system as described above and in the following may be features of the method.

A third aspect of the invention relates to computer program element, which when executed on a controller of a cardiac CT imaging system, instructs the controller to carry out the steps of the method as described above and in the following.

A fourth aspect of the invention relates to a computer-readable medium on which a computer program element is stored, which, when executed on a controller of a cardiac CT imaging system, instructs the controller to carry out the steps of the method as described above and in the following. A computer-readable medium may be, among others, a floppy disk, a hard disk, an USB (Universal Serial Bus) storage device, a RAM (Random Access Memory), a ROM (Read Only memory) and an EPROM (Erasable Programmable Read Only Memory). A computer readable medium may also be a data communication network, e.g. the Internet, which allows downloading a program code.

BRIEF DESCRIPTION OF THE DRAWINGS

Exemplary embodiments of the invention will now be described with reference to the following drawings, which are not necessarily to scale, wherein FIGS. 1A and 1B each schematically show acquisition time periods as a function the heart phase.

In principle, identical and/or similar elements are provided with the same reference symbols in the figures.

DETAILED DESCRIPTION OF EMBODIMENTS

Figure 1A:
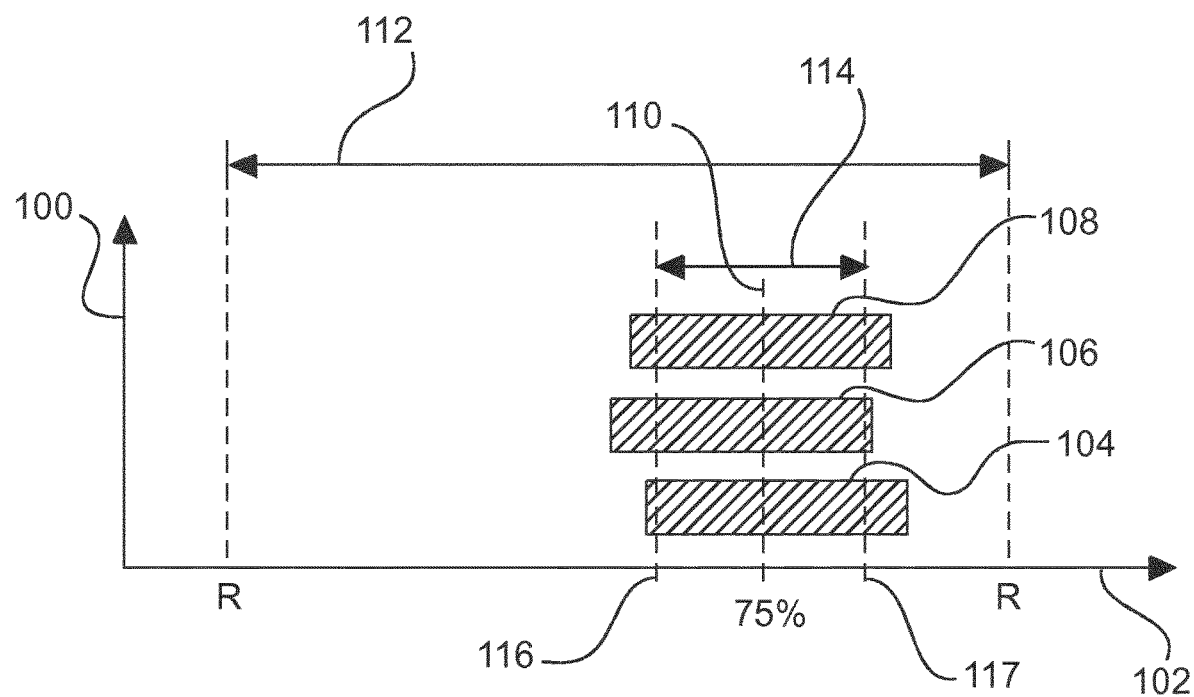
Figure 1B:
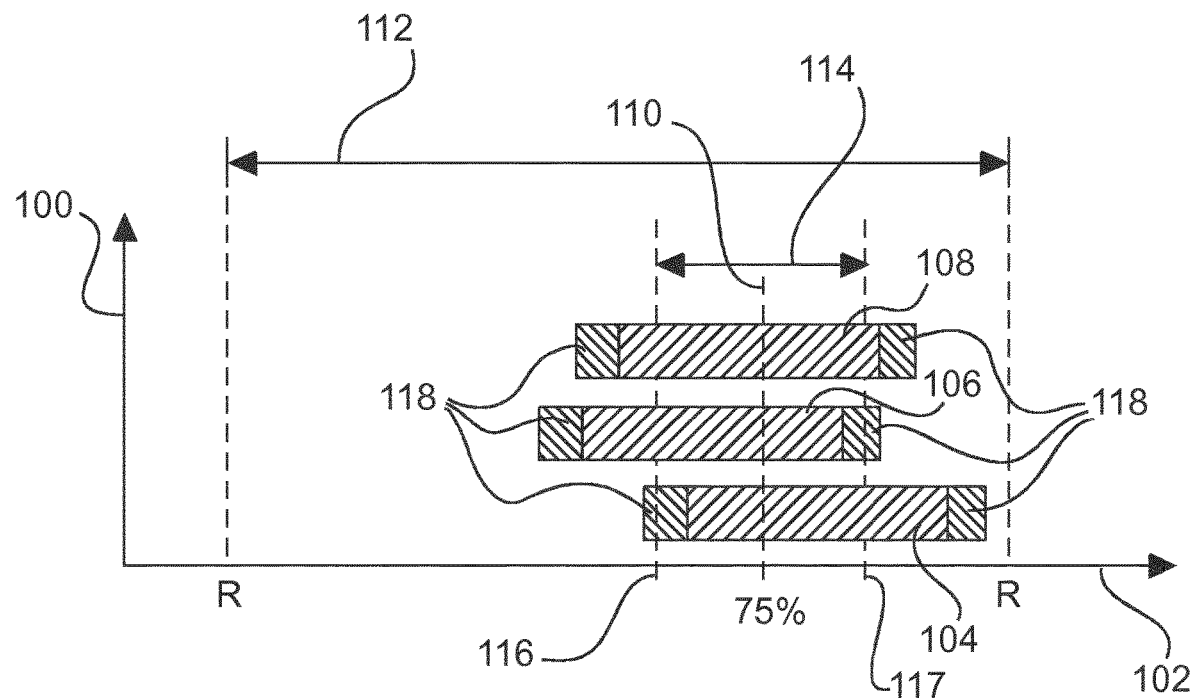

FIGS. 1A and 1B each schematically show acquisition time periods as a function of the heart phase φ. FIGS. 1A and 1B thereby illustrate findings and insights, on which the present invention is based. More specifically, the y-axis 100 in FIGS. 1A and 1B, respectively, depicts a number of shoots, i.e., acquisition time intervals and/or acquisition time periods, of a step-and-shoot scan performed with a cardiac CT imaging system, and the x-axis 102 depicts the heart phase φ. Therein, a total number of three shots 104, 106, 108 of the step-and-shoot scan are shown.

Generally, prospective electrocardiography-triggering (ECG-triggering) of the CT imaging system has been applied during acquisition of projection data, which was started at a certain time after an R-peak of a heart cycle 112 was determined based on ECG data and/or based on a dataset comprising ECG data. Therein, the heart cycle 112 is determined as time period between two consecutive R-peaks in the ECG data.

In FIGS. 1A and 1B the aimed heart phase, i.e. the heart phase, in which projection data should have been acquired was at 75% of the heart cycle 112, as indicated by line 110 in FIGS. 1A and 1B, respectively.

Generally, an optimum acquisition time period $\Delta T_{ac}$, illustrated as arrow or range 114 centered around the aimed heart phase of 75%, would allow optimal reconstruction of the heart from the projection data, because sufficient projection data centered around the aimed heart phase as marked by dashed lines 116, 117 in FIGS. 1A and 1B would be available.

However, depending on a stability and/or a variability of the heart rate, the acquisition time period $\Delta T_{ac}$ may have to be increased in order to be able to acquire sufficient projection data over the required range 114. An instability and/or variability of the heart rate is illustrated in FIGS. 1A and 1B by a slight shift between bars illustrating the respective three shots 104, 106, 108, wherein the bars of the shots 104, 106, 108 basically illustrate the ECG-triggered acquisition time periods $\Delta T_{ac}$ for each of the shots 104, 106, 108. Further, a heart rate may not be perfectly constant, i.e. the R-R time intervals 112 may vary. This effect would result in different lengths of the bars of each shot 104, 106, 108 meaning that different acquisition time periods $\Delta T_{ac}$ would be required for each of the shoots 104, 106, 108. For the sake of a clear illustration, this effect is neglected in FIGS. 1A and 1B.

Referring to FIG. 1A, a rather stable heart rate is illustrated, wherein the ECG-triggered acquisition time periods $\Delta T_{ac}$ are nicely centered around the aimed heart phase of φ=75% of the R-R time interval 112. For all three shots 104, 106, 108 the projection data in the required range 114 are available. This would allow an optimum reconstruction of the heart based on the projection data. In case of acquiring images with a CT imaging system comprising a rotatable gantry, the projection data acquired may thus cover a sufficient angle range in order to fully reconstruct the heart from subsets of these projection data centered at the aimed heart phase.

Referring to FIG. 1B, a situation is illustrated, in which the heart rate variation and/or the variability of the heart rate is larger than in case of FIG. 1A. Accordingly, the shifts between the acquisition time periods $\Delta T_{ac}$ for each of the shots 104, 106, 108 are larger than in FIG. 1A. When using the same acquisition time periods $\Delta T_{ac}$ as in case FIG. 1A, not all required data may be acquired and/or measured. Therefore, the overall acquisition time periods $\Delta T_{ac}$ need to be increased by the padding time $\Delta T_{pad}$ which is indicated by the shaded regions 118 for each shot 104, 106, 108 in FIG. 1B. By increasing the acquisition time period with the padding time, it may be ensured that sufficient projection data may be acquired in order to allow a reconstruction of the heart based on subsets of these projection data centered around the aimed heart phase. Again, in case of a rotatable gantry, the required projection data may refer to an angle range.

Summarizing, for a very stable heart rate the projection data acquired for each shot 104, 106, 108 may have to encompass an angle range only slightly larger than the range required for reconstruction, while for an instable heart rate data have to be acquired over a larger time period, i.e. with a larger safety margin called padding and/or padding time, in order to make sure that the required heart phase range is covered, which may allow larger adjustments of the projection angle ranges used for the reconstruction.

Figure 2:
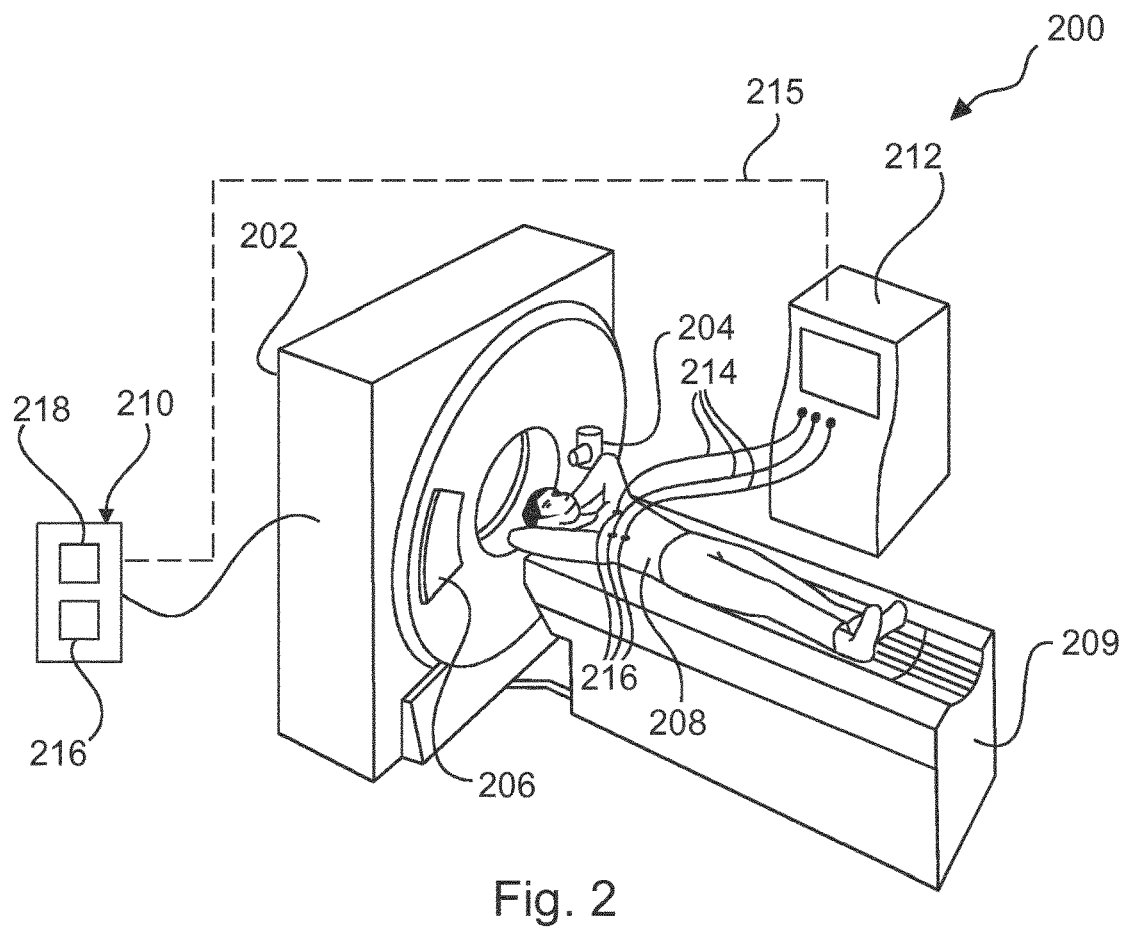
FIG. 2 schematically shows a cardiac CT imaging system according to an embodiment of the invention.

FIG. 2 schematically shows a cardiac CT imaging system 200 according to an embodiment of the invention.

The CT imaging system 200 comprises a rotatable gantry 202 with an X-ray radiation source 204 that projects a beam of X-rays 16 toward an X-ray detector 206. The detector 206 may be designed as a detector array comprising a plurality of X-ray sub-detectors. The radiation source 204 and the detector 206 are arranged on opposite sides of the gantry 202. By means of the detector 206 projected X-rays that pass through a patient 208 are sensed and/or detected, wherein patient 208 is arranged on a movable table 209.

By way of example, the detector 206 may comprise several rows of sub-detectors for the acquisition of slices of acquisition data in a single gantry rotation. Each of the sub-detectors of detector 206 may produce an electrical signal that represents an intensity of an impinging X-ray beam and hence represents the attenuated beam when passed through the patient 208. During a scan to acquire X-ray projection data, gantry 202 and the components mounted thereon rotate about a center of rotation and/or a longitudinal axis of the patient 208.

The CT imaging system further comprises a controller 210, which may among others govern rotation of gantry 202 and the operation of the X-ray source 204 and the detector 206. The controller 210 may for instance refer to a control unit, a control arrangement and/or a computer.

Moreover, the CT imaging system 200 comprises an electrocardiograph 212 and/or an ECG device 212 for acquiring electrocardiography data of patient 208. For this purpose, the ECG device 212 is connected via wires 214 and electrodes 216 to the patient 208.

Further, the ECG device 212 is connected via a line 215 to the controller 210, which is configured for receiving and/or processing ECG data acquired by means of the ECG device 212.

The imaging system 200 further comprises a data storage 216 and/or a data storage device 216 for storing ECG data and/or a dataset comprising ECG data. The data storage 216 may be connected to the controller 210, such that the controller 210 can process these ECG data.

By means of the ECG device 212 and the controller 210 prospective electrocardiography-triggering (ECG-triggering) of the imaging system 200 is accomplished. This may mean, that a data acquisition by means of the imaging system 200 may be started at a certain time after an R-peak of a heart cycle, which is determined by means of the controller 210 based on ECG data and/or based on a dataset comprising ECG data. In other words, at a certain time after an R-peak, the controller 210 may trigger the radiation source 204 and/or the detector 206 in order to acquire projection data of the heart over a certain acquisition time period at a certain heart phase, such as e.g. 75% of a heart cycle, in which motion of the heart is minimal.

In more detail, ECG data and/or cardiac data of the patient 208 are acquired by means of the ECG device 212. These data may be stored as a dataset in the data storage 216 and/or the data may be processed in real-time by the controller 210. The controller 210 may correlate the ECG data to determine the phases of the heart cycle, to determine R-peak times and/or to determine a heart rate. Before scanning commences and/or during scanning, the controller 210 determines the acquisition time period $\Delta T_{ac}$, i.e. the time period and the time point, during which projection data are to be acquired by statistically analyzing the determined R-peak times based on the ECG dataset, thereby determining a variability of the heart rate. This is explained in more detail in the summary section and with reference to an exemplary embodiment described in FIG. 3. Further, the controller 210 is configured to automatically adjust the acquisition time period of the CT imaging system 200 based on the determined variability of the heart rate. This may be done before and/or during a scan.

A starting point for data acquisition may be chosen by the controller 210 during quiescent periods between two consecutive R-peaks of the cardiac cycle or heart cycle, respectively. During these quiescent periods, the heart is relatively still and, therefore, data acquisition preferably is performed during these portions of the heart cycle in order to minimize motion artifacts in the final reconstructed image.

For image reconstruction, the imaging system 200 may further comprise an image reconstructor 218 receiving sampled and digitized X-ray data from detector 206. The reconstructor 218 may perform high-speed reconstruction and the reconstructed image may be stored on the data storage 216.

Generally, the controller 210 of the imaging system 200 is configured to perform any step of the method for operating the CT imaging system 200 as described above and in the following.

It is to be noted that the invention is likewise applicable to helical scan acquisition with tube current modulation.

Figure 3:
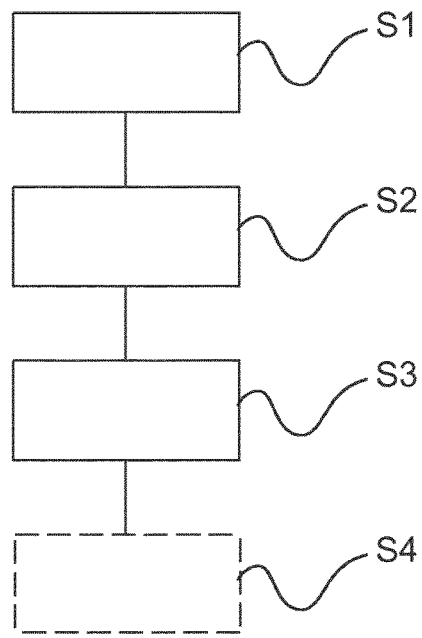
FIG. 3 schematically shows a flow chart illustrating steps of a method for operating a cardiac CT imaging system according to an embodiment of the invention.

FIG. 3 schematically shows a flow chart illustrating steps of a method for operating a cardiac CT imaging system 200 in coronary CT with prospective electrocardiography-triggering of the imaging system 200 according to an embodiment of the invention.

In a first step S1 of the method, a plurality of R-peak times $t_i$ is determined, by means of the controller 210, from a dataset of electrocardiography data, which were acquired by the ECG device 212. In a further step S2, a variability of a heart rate is determined, by means of the controller 210, by statistically analyzing the determined R-peak times $t_i$. In a third step S3 an acquisition time period $\Delta T_{ac}$ of the CT imaging system 200 for acquiring projection data is automatically adjusted based on the determined variability of the heart rate. Also step S3 is performed by means of the controller 210.

Generally, step S2 and/or statistically analyzing the R-peak times $t_i$ comprises determining a plurality of heart cycle times $\Delta T_i = t_i - t_{i-1}$ based on the determined R-peak times $t_i$ and/or determining a plurality of differences of consecutive heart cycle times $\Delta T_{i+1} - \Delta T_i$ based on the determined R-peak times $t_i$.

Further, step S2 and/or statistically analyzing the R-peak times $t_i$ further comprises determining a standard deviation $\sigma = \text{std}(\{t_i - t_{i-1} | i=1 \ldots N-1\})$ of the determined plurality of heart cycle times, and/or determining a standard deviation $\sigma = \text{std}(\{\Delta T_{i+1} - \Delta T_i | i=2 \ldots N-1\})$ of the determined plurality of differences of consecutive heart cycle times.

Optionally, the method comprises a step S4 of determining a padding time $\Delta T_{pad}$ based on a multiplication of the standard deviation of the plurality of heart cycle times and/or the standard deviation of the plurality of differences of consecutive heart cycle times with a phase factor $\gamma$ relating to a predefined heart phase $\varphi$ of the heart cycle. By way of example, $\gamma$ may be 0.75 relating to a heart phase $\varphi$ of 75% of the heart cycle. Also $\gamma = 0.4$ and $\varphi = 40\%$ may be feasible, as the heart may move only little at these phases.

Further, optionally, in step S4 the padding time $\Delta T_{pad}$ may be determined based on a multiplication of the standard deviation of the plurality of heart cycle times and/or the standard deviation of the plurality of differences of consecutive heart cycle times with a confidence factor $\mu$ indicative of a probability of acquiring projection data sufficient for a reconstruction of the heart at the predefined heart phase $\varphi$.

In the following an example of the method described above is explained in detail and with exemplary values.

When starting an ECG-triggered CT scan the ECG data is acquired for a certain time and R-peak times $t_i$, ($i=1, \ldots, N$) are determined. When the heart rate would be perfectly constant, an acquisition time period of projection data centered around the aimed heart phase and for the angular range required by the reconstruction and/or the reconstructor 218 would be sufficient to guarantee a reconstruction at the aimed heart phase $\varphi$. If $\Delta T_{ac}$ is the acquisition time period needed for this, the projection data for a 75% heart phase $\varphi$ would be acquired at an instant of time and in a time interval of $$t_i + 0.75(t_i - t_{i-1}) + \left[-\frac{\Delta Tac}{2}, \frac{\Delta Tac}{2}\right].$$

The minimum acquisition time period $\Delta T_{ac,min}$ is determined by the required angular range $\Delta \Phi$, over which projection data potentially have to be acquired, and the rotation time $t_{rot}$ of the gantry 202

$$\Delta T_{ac,min} = t_{rot} \cdot \frac{\Delta \Phi}{360°}.$$

However, the heart rate may vary. An analysis of its variation and/or the variability of the heart rate allows to optimize the acquisition. A measure for the variability of the heart rate would be the standard deviation of the determined R-peak times.

Alternatively, the standard deviation of differences of consecutive heart cycle times may be used as exemplary used in the following.

The standard deviation of differences of consecutive heart cycle times $\Delta T_i = t_i - t_{i-1}$ determined from the first N R-peak times $t_i$, may be expressed as follows:

$$\sigma = \text{std}(\{\Delta T_{i+1} - \Delta T_i | i = 2, \ldots, N-1\})$$

Assuming that a Gaussian distributed random variable X describes the variation of these differences, one can estimate the probability distribution of the next R-peak time by:

$$t_{i+1} = t_i + (t_i - t_{i-1}) + X.$$

The probability distribution of the $\varphi = 75\%$ heart phase, i.e. the phase point $t_i^{75\%}$ within the next heart cycle is correspondingly a Gaussian function with a standard deviation of $0.75\sigma$, which may be expressed as follows:

$$p(t = t_i^{75\%}) = C \exp\left(\frac{-(t - (t_i + 0.75(t_i - t_{i-1})))^2}{2(0.75\sigma)^2}\right),$$

where C is a normalization constant.

The padding time $\Delta T_{pad}$, i.e., the additional acquisition time needed to achieve sufficient data centered around the 75% heart phase and/or the corresponding phase point $t_i^{75\%}$ can be calculated from the quantiles of this distribution. The 2.5 and 97.5 percentiles of a Gaussian distribution with standard deviation c are $-1.96\sigma$ and $+1.96\sigma$. Thus a reconstruction at the 75% heart phase can be achieved in 95% of all cases by increasing the above mentioned acquisition time period required for the reconstruction both at the beginning and the end by $\Delta T_{pad} = \Delta T^{95\%} = 1.96 \cdot 0.75\sigma$. Thus, the optimum acquisition period is $$t_i + 0.75(t_i - t_{i-1}) + \left[-\frac{\Delta Tac}{2} - \Delta T^{95\%}, \frac{\Delta Tac}{2} + \Delta T^{95\%}\right].$$

This optimization can be performed in real time just before the scan. It is even possible to take heart rate variations during the scan into consideration, such that changing the acquisition time period from shot to shot is possible. It is therefore advantageous with respect to the estimation of the padding time by the CT user, which has to be based on ECG data formerly acquired and on the experience of the user, as it is done in state-of-the art approaches.

The above described method is likewise applicable to helical scan acquisition with tube current modulation. Here the time periods with full tube current can be optimized based on the statistical analysis of the ECG.

Moreover, slight deviations of the heart phase from the aimed heart phase, e.g. 75%, observed and/or occurring during the scan, may have no considerable impact on the image quality. Therefore, acquisition time periods as calculated with the above confidence level of 95% may by far not lead to unacceptable image quality in 5% of all cases. Thus, using a lower confidence level, such as e.g. 70%-95%, may lead to a better trade-off between radiation dose and image quality.

Moreover, it may be advantageous to define a range of acceptable heart phases, e.g., 72-78% of the R-R cycle, or other ranges as already described above. This requirement may lead to a different calculation of the padding time by the controller 210 such as e.g. $\Delta T_{Pad} = \max(a \cdot \sigma - b, 0)$, where the constant $\alpha$ may depend on the confidence level and the aimed heart phase and b on the size of the interval of acceptable heart phases.

In other words, the method as described above may comprise, e.g. in the optional step S4, comparing the standard deviation of the plurality of heart cycle times and/or the standard deviation of the plurality of differences of consecutive heart cycle times with a threshold value, wherein the acquisition time period $\Delta T_{ac}$ may only increased by the padding time $\Delta T_{pad}$ if the standard deviation of the plurality of heart cycle times and/or the standard deviation of the plurality of differences of consecutive heart cycle times exceeds the threshold value.

It is to be noted that any functional modules as described above may be implemented as programmed software modules or procedures, respectively; however, one skilled in the art will understand that the functional modules may be implemented fully or partially in hardware.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art and practicing the claimed invention, from a study of the drawings, the disclosure, and the appended claims. In the claims, the word "comprising" does not exclude other elements or steps, and the indefinite article "a" or "an" does not exclude a plurality. A single processor or controller or other unit may fulfil the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. A method for operating a cardiac CT imaging system in coronary CT with prospective electrocardiography-triggering of the imaging system, the method comprising:
   determining a plurality of R-peak times from a dataset of electrocardiography data;
   determining a variability of a heart rate by statistically analyzing the determined R-peak times; and
   automatically adjusting an acquisition time period of the CT imaging system for acquiring projection data based on the determined variability of the heart rate,
   wherein automatically adjusting the acquisition time period comprises automatically adjusting a length of the acquisition time period based on the determined variability of the heart rate.

2. The method according to claim 1, wherein statistically analyzing the R-peak times comprises:
   determining a plurality of heart cycle times based on the determined R-peak times.

3. The method according to claim 2, wherein statistically analyzing the R-peak times further comprises:
   determining a standard deviation of the determined plurality of heart cycle times.

4. The method according to claim 3, further comprising:
   determining a padding time based on at least one of: a multiplication of the standard deviation of the plurality of heart cycle times; and the standard deviation of the plurality of differences of consecutive heart cycle times with a phase factor relating to a heart phase of the heart cycle.

5. The method according to claim 4,
   wherein the phase factor is between 0.65 and 0.85 relating to a heart phase of 65% to 85%.

6. The method according to claim 4,
wherein the phase factor is between 0.3 and 0.5 relating to a heart phase of 30% to 50%.

7. The method according to claim 4, further comprising:
determining the padding time based on at least one of: a multiplication of the standard deviation of the plurality of heart cycle times; and the standard deviation of the plurality of differences of consecutive heart cycle times with the phase factor and a confidence factor indicative of a probability of acquiring projection data sufficient for a reconstruction of the heart at the heart phase.

8. The method according to claim 4, further comprising:
comparing at least one of: the standard deviation of the plurality of heart cycle times; and the standard deviation of the plurality of differences of consecutive heart cycle times with a threshold value;
wherein the acquisition time period is only increased by the padding time if at least one of: the standard deviation of the plurality of heart cycle times; and the standard deviation of the plurality of differences of consecutive heart cycle times exceeds the threshold value.

9. The method according to claim 7,
wherein the confidence factor is determined under the assumption that a random variable describes at least one of: a variation of the heart cycle times; and a variation of the plurality of differences of consecutive heart cycle times.

10. The method according to claim 9,
wherein the random variable is a Gaussian distributed random variable.

11. The method according to claim 10,
wherein the confidence factor is determined based on percentiles of a Gaussian function describing a probability distribution of a heart phase within the heart cycle.

12. The method according to claim 11,
wherein the percentiles of the Gaussian function are 2.5% and 97.5%.

13. The method according to claim 1, wherein statistically analyzing the R-peak times comprises:
determining a plurality of differences of consecutive heart cycle times based on the determined R-peak times.

14. The method according to claim 13, wherein statistically analyzing the R-peak times further comprises:
determining a standard deviation of the determined plurality of differences of consecutive heart cycle times.

15. The method according to claim 7, wherein the confidence factor is determined based on a confidence level of a probability distribution assumed for a random variable describing at least one of: a variation of the heart cycle times; and a variation of the plurality of differences of consecutive heart cycle times.

16. A cardiac CT imaging system, comprising:
an X-ray radiation source;
an X-ray detector; and
controller circuitry;
wherein the controller circuitry is configured to:
determine a plurality of R-peak times from a dataset of electrocardiography data;
determine a variability of a heart rate by statistically analyzing the determined R-peak times; and
automatically adjust an acquisition time period of the CT imaging system for acquiring projection data based on the determined variability of the heart rate,
wherein automatically adjusting the acquisition time period comprises automatically adjusting a length of the acquisition time period based on the determined variability of the heart rate.

17. The cardiac CT imaging system of claim 16, wherein statistically analyzing the R-peak times comprises:
determining a plurality of heart cycle times based on the determined R-peak times.

18. The cardiac CT imaging system of claim 17, wherein statistically analyzing the R-peak times further comprises:
determining a standard deviation of the determined plurality of heart cycle times.

19. The cardiac CT imaging system of claim 16, wherein statistically analyzing the R-peak times comprises:
determining a plurality of differences of consecutive heart cycle times based on the determined R-peak times.

20. A non-transitory computer-readable medium having one or more executable instructions stored thereon, which, when executed by processor circuitry, cause the processor circuitry to conduct a method for operating a cardiac CT imaging system in coronary CT with prospective electrocardiography-triggering of the imaging system, the method comprising:
determining a plurality of R-peak times from a dataset of electrocardiography data;
determining a variability of a heart rate by statistically analyzing the determined R-peak times; and
automatically adjusting an acquisition time period of the CT imaging system for acquiring projection data based on the determined variability of the heart rate,
wherein automatically adjusting the acquisition time period comprises automatically adjusting a length of the acquisition time period based on the determined variability of the heart rate.

* * * * *